United States Patent [19]

Rei et al.

[11] Patent Number: 4,761,247

[45] Date of Patent: Aug. 2, 1988

[54] PHENOL-STABILIZED MICROBIOCIDAL COMPOSITIONS

[75] Inventors: Nuno M. Rei, Boxford; Lawrence P. Grant, Salem, both of Mass.

[73] Assignee: Morton Thiokol, Inc., Chicago, Ill.

[21] Appl. No.: 22,456

[22] Filed: Mar. 6, 1987

[51] Int. Cl.$^4$ .................... B01F 1/00; A01N 33/00; A01N 55/02; A01N 43/36

[52] U.S. Cl. ................... 252/364; 252/308; 252/400.54; 252/404; 424/405; 514/412; 514/504; 514/722; 514/730; 514/746; 523/122

[58] Field of Search ............... 514/785, 412, 504, 722, 514/730; 252/308, 364, 404, 400.54; 523/122; 424/405

[56] References Cited

U.S. PATENT DOCUMENTS

| | | | |
|---|---|---|---|
| 3,288,674 | 11/1966 | Yeager | 167/42 |
| 3,360,431 | 12/1967 | Yeager | 167/30 |
| 3,689,449 | 9/1972 | Yeager et al. | 260/33.4 P |
| 4,049,822 | 9/1977 | Rei et al. | 514/504 |
| 4,624,679 | 11/1986 | McEntee | 523/122 |
| 4,663,077 | 5/1987 | Rei et al. | 252/364 |
| 4,683,080 | 7/1987 | Rei et al. | 514/412 |

*Primary Examiner*—Herbert J. Lilling
*Attorney, Agent, or Firm*—Gerald K. White; Wayne E. Nacker

[57] ABSTRACT

Solutions of microbiocides in cosolvents having alkanol moieties and concentrate compositions of carriers, microbiocides and cosolvents having alkanol moieties are stabilized against UV-catalyzed oxidation by the addition of phenolic antioxidants. The solutions or concentrate compositions are added to polymeric resins and formed, e.g., by fusion, into polymer compositions exhibiting microbiocidal properties.

35 Claims, No Drawings

PHENOL-STABILIZED MICROBIOCIDAL COMPOSITIONS

BACKGROUND OF THE INVENTION

1. Field of the Invention

This invention relates to liquid microbiocidal solutions containing a solvent having an alkanol moiety, a microbiocidal compound dissolved in the solvent and a phenolic antioxidant.

This invention also relates to compositions comprising a carrier, a microbiocidal compound, a consolvent for the microbiocidal compound having an alkanol moiety which is also compatible with the carrier (solvent) and a phenolic antioxidant.

The present invention further relates to a process for imparting microbiocidal properties to polymer compositions comprising adding to the polymer composition a liquid microbiocidal solution comprising a cosolvent having an alkanol moiety, a microbiocidal compound dissolved in the cosolvent and a phenolic antioxidant.

This invention further relates to compositions comprising a solution of a liquid plasticizer for vinyl resins, a biologically effective amount of a microbiocidal compound, a cosolvent having an alkanol moiety for the microbiocidal compound and liquid plasticizer, and a phenolic antioxidant.

This invention further relates to vinyl resin compositions comprising an admixture of a vinyl resin and a vinyl resin plasticizer containing, in an amount sufficient to impart microbiocidal properties to the vinyl resin composition, a microbiocidal compound dissolved in a cosolvent having an alkanol moiety and a phenolic antioxidant.

2. Prior Art

It is presently common practice to protect polymer or plastic compositions from microbiocidal, e.g., bacterial or fungal, attack by incorporating microbiocidal compounds into the polymer or plastic compositions. The resulting polymer compositions prevent the deterioration of articles formed from the polymer compositions which is due to microbiological attack on the plasticizers or other polymer additives which are normally incorporated into the polymer compositions to impart desirable physical properties to the articles and to facilitate forming of the articles.

Many of the available microbiocidal materials are solid, and in order to incorporate them homogeneously into polymer compositions, it is necessary to first mix them with liquids which solubilize or disperse the microbiocidal materials uniformly and, thereafter, mix the thus-formed liquid compositions with the polymers. Unfortunately, the solubilities of many of the microbiologically active compounds in the more common solvents are quite low. Therefore, it is either difficult to incorporate a sufficiently high concentration of a microbiocidal compound with a polymer or, if a sufficiently high concentration of the microbiocidal compound can be incorporated in the polymer, an undesirably high concentration of the solvent must also be incorporated into the polymer, compromising the desirable characteristics of the polymer composition.

Attempts to solve these problems have met with varying, often limited, success. For example, U.S. Pat. No. 3,288,674 issued Nov. 29, 1966 to Yeager and U.S. Pat. No. 3,689,449 issued Sept. 5, 1972 to Yeager and Wilson disclose the use of solvents having a labile hydrogen, preferably nonyl phenol, to dissolve microbiocidally active phenoxarsine compounds, the resulting solutions being subsequently incorporated into polymeric resin compositions. Unfortunately, the solubilities of phenoxarsines in nonyl phenol are limited to low concentrations which necessitates incorporating nonyl phenol in the resin at higher concentrations than desirable in order to attain the desired phenoxarsine levels in the polymeric resins.

U.S. Pat. No. 3,360,431 issued December 1967 to Yeager discloses the use of labile hydrogen-containing solvents, preferably nonyl phenol, to dissolve microbiocidally active arsenobenzene compounds for subsequent addition to polymeric resin compositions.

U.S. Pat. No. 4,624,679 describes the advantageous use of aryl alkanols, such as benzyl alcohol, as cosolvents for microbiocidal agents which are to be formulated into solutions with carriers, such as plasticizers and/or other processing aids. The application teaches that aryl alkanol cosolvents, such as benzyl alcohol, increase the levels of microbiocides, particularly phenoxarsines, which can be dissolved per amount of carrier.

Although aryl alkanols have proven to be advantageous cosolvents with respect to the amounts of microbiocides which may be carried into a polymer per amount of cosolvent, there has been found to be a problem with respect to shelf-life. Compounds that contain a carrier, such as a plasticizer, a microbiocidal agent, such as a phenoxarsine, and an aryl alyanol cosolvent exhibit instability due to what appears to be a UV-catalyzed oxidation of the microbiocide. Oxidation of the microbiocide, of course, reduces the effective concentration of the microbiocide; however, this is a relatively minor problem. A major problem with microbiocide oxidation is precipitation of the oxidation products; crystals of oxidation products are frequently found to occur in compositions comprising plasticizers, microbiocides and aryl alkanols.

Crystals of oxidation products are problematic in at least two important respects. Crystals in the composition are detrimental to processing of a polymer and are detrimental to the final product. In addition, crystalization of oxidation products provides nuclei for crystalization of the microbiocide itself, and more microbiocide may be lost through such crystalization than through direct oxidation of the microbiocide.

The problem of UV-catalyzed oxidation and subsequent crystalization and precipitation is found to not only occur with aryl alkanols but generally when using solvents containing an alkanol group, such as isodecyl alcohol. It is, therefore, a general object of the invention to provide compositions containing a microbiocide and a cosolvent therefore which are resistant to UV-catalyzed oxidation of the microbiocide.

SUMMARY OF THE INVENTION

In accordance with the present invention, there are provided liquid microbiocidal solutions comprising a cosolvent having an alkanol moiety, a microbiocidal compound dissolved in the cosolvent, and a phenolic antioxidant.

Also provided, in accordance with this invention, are compositions comprising a carrier, such as a plasticizer or other processing aid, and, in an amount at least sufficient to impart microbiocidal properties to the composition, a microbiocidal compound which is present in the carrier as the solute in a cosolvent having an alkanol moiety plus a phenolic antioxidant.

There is also provided in accordance with the present invention a process for imparting microbiocidal properties to a polymer composition comprising adding to the polymer composition a liquid microbiocidal solution comprising a cosolvent having an alkanol moiety and, in an amount sufficient to impart microbiocidal properties to the polymer composition, a microbiocidal compound dissolved therein plus a phenolic antioxidant.

There is further provided in accordance with this invention a process for imparting microbiocidal properties to a polymer composition comprising adding to the polymer composition a composition comprising a carrier and, in an amount at least sufficient to impart microbiocidal properties to the polymer composition, a microbiocidal compound which is present in the carrier as the solute in a cosolvent having an alkanol moiety, the composition further comprising a phenolic antioxidant. The product of this process is also included in the invention.

There are also provided, in accordance with this invention, plasticizing compositions capable of plasticizing vinyl resins and imparting microbiocidal properties thereto, such a composition comprising a liquid plasticizer for vinyl resins and, in an amount sufficient to impart microbiocidal properties to a vinyl resin plasticized with the plasticizing composition, a microbiocidal compound present in the plasticizer as the solute in a cosolvent having an alkanol moiety, the composition further comprising a phenolic antioxidant, said solute, cosolvent and antioxidant being a liquid uniformly distributed in said plasticizer to form a single phase system.

There are further provided, in accordance with this invention, vinyl resin compositions, each comprising an admixture of vinyl resin and a vinyl resin plasticizer, the vinyl resin composition containing, in an amount sufficient to impart microbiocidal properties to the vinyl resin composition, a microbiocidal compound, a cosolvent for the microbiocidal compound having an alkanol moiety plus a phenolic antioxidant.

DESCRIPTION OF THE PREFERRED EMBODIMENTS

The present invention is specifically directed to applications in which the microbiocidal compound is not sufficiently soluble in the resin itself to be dissolved directly therein and is also not sufficiently soluble in a carrier, such as a plasticizer or other processing aid, to be provided to the resin through solution in the carrier alone. In such case, an organic solvent is used which is a cosolvent for the microbiocidal compound and the resin or a cosolvent for the microbiocidal compound and the carrier, e.g., the plasticizer. Specifically, the present invention is directed to applications in which the primary cosolvent has alkanol moieties which are found to dissolve relatively high levels of the most commonly used microbiocidal compounds.

Cosolvents used in accordance with the invention are selected for solubilizing a high concentration of the microbiocide and maintaining the microbiocide in solution when a solution of the cosolvent and the microbiocide are admixed with a carrier, such as a plasticizer. Of interest herein are cosolvents having alkanol moieties, including alcohols having straight or branched, saturated or unsaturated carbon chains of at least about 8 carbon atoms and also aryl alkanols, such as benzyl alcohol.

The aryl alkanols useful as cosolvents in the practice of this invention are compounds which have an hydroxyl group attached to an aromatic ring through an alkyl group. That is, the aryl alkanols of this invention contain an aromatic ring to which is attached a group having the formula —R—OH where R is a straight or branched-chain alkyl group, preferably having 1-6 carbon atoms, more preferably 1-3 carbon atoms and more preferably 1 carbon atom. The alkylene group may be unsubstituted or substituted with other groups such as, for example, halogens, amines, hydroxyl, or alkoxyl groups.

The term aryl as used herein refers to aromatic rings which may be substituted with functional groups. Examples of such aromatic rings includes, but are not limited to, benzene, naphthalene, and biphenyl rings. When the aryl group is substituted with functional groups, it may have any number of groups attached to the aromatic ring, it being required only that the types of functional groups, their position on the ring and/or their number do not interfere with the aryl alkanol's ability to dissolve the microbiocidal compound or, if it is to be employed as part of a polymer composition, its compatibility with the polymer. Examples of such functional groups on the aryl rings include, but are not limited to, halogen, aryloxy, amino, hydroxyl, alkoxyl, and nitro groups.

The aryl alkanols useful as cosolvents in the practice of this invention may be further defined by the following general formula:

A—R—OH, wherein A is an aromatic ring, preferably benzene, which may be unsubstituted, e.g., phenyl, or substituted with one or more halo, aryloxy, amino, hydroxyl, alkoxyl or nitro groups, and R is a straight or branched chain alkyl group, preferably having 1-6 carbon atoms, which may be unsubstituted or substituted with halo, amino, hydroxyl, or alkoxyl groups.

The aryl alkanols which are useful as cosolvents in the practice of the present invention are those in which the hydroxyl group of the alkanol is a primary, secondary or tertiary alcohol. The preferred aryl aklanols are those in which the hydroxy group is a primary alcohol.

Examples of aryl alcohols which may be employed as cosolvents in accordance with this invention include, but are not limited to, the following:

$C_6H_5-CH_2-OH$
benzyl alcohol;

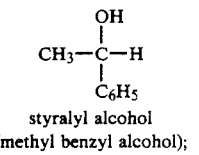
styralyl alcohol
(methyl benzyl alcohol);

$HO-CH_2-CH_2-C_6H_5$
phenethyl alcohol;

$HO-CH_2-CH_2-CH_2-C_6H_5$
3-phenyl-1-propanol;

-continued

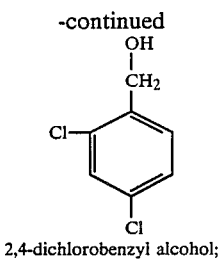

2,4-dichlorobenzyl alcohol;

and

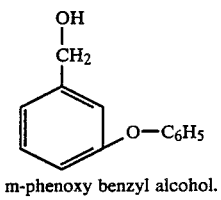

m-phenoxy benzyl alcohol.

Of these aryl alkanols, benzyl alcohol, 2,4-dichlorobenzyl alcohol, and styralyl alcohol are preferred cosolvents, benzyl alcohol being an especially preferred cosolvent.

The aryl alkanols exemplified above are all liquids with the exception of 2,4-dichlorobenzyl alcohol, which is a solid. This compound has quite surprisingly been found to act as a cosolvent for those microbiocidal compounds which are liquids. If the 2,4-dichlorobenzyl alcohol is heated slightly it melts and then can be combined with the microbiocidal compound to form a stable solution. The 2,4-dichlorobenzyl alcohol also exhibits microbiocidal activity by itself. Thus, it can be dissolved in another aryl alkanol, for example, benzyl alcohol, to produce a microbiocidal solution in accordance with this invention.

Also suitable as cosolvents in accordance with the invention are relatively hydrophobic alcohols having branched or straight, saturated or unsaturated carbon chains of 8 carbon atoms or more. Preferably such alcohols are primary alcohols. A preferred alcohol cosolvent is isodecyl alcohol. Other suitable alcohol solvents include, but are not limited to 2-ethyl hexanol and dodecyl alcohol.

A wide variety of microbiocidal compounds are useful in the practice of this invention. A microbiocidal compound should be compatible with the processing aid and the polymer with which it is to be used.

Examples of the types of microbiocidal compounds which may be employed in this invention include, but are not limited to, phenoxarsines (including bisphenoxarsines), phenarsazines (including bisphenarsazines), maleimides, isoindole dicarboximides, having a sulfur atom bonded to the nitrogen atom of the dicarboximide group, halogenated aryl alkanols and isothiazolinone compounds.

The microbiocidal phenoxarsine and phenarsazine compounds useful in the compositions of this invention include compounds represented by the formulas:

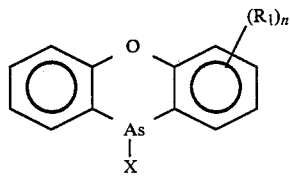

and

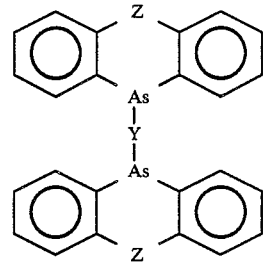

where X is halogen or thiocyanate, Y is oxygen or sulfur, Z is oxygen or nitrogen, R is halo or lower alkyl, and n is 0 to 3. Examples of these phenoxarsines and phenarsazines include, but are not limited to, 10-chlorophenoxarsine; 10-iodophenoxarsine; 10-bromophenoxarsine; 4-methyl10-chlorophenoxarsine; 2-tert-butyl-10-chlorophenoxarsine; 1,4-dimethyl-10-chlorophenoxarsine; 2-methyl-8,10-dichlorophenoxarsine; 1,3,10-trichlorophenoxarsine; 2,6,10-trichlorophenoxarsine; 1,2,4,10-tetrachlorophenoxarsine; 10,10'-oxybisphenoxarsine (OBPA); 10-thiocyanato phenoxarsine; 10,10'-thiobisphenoxarsine; 10,10'-oxybisphenarsazine and 10,10'-thiobisphenarsazine.

The microbiocidal maleimide compounds useful in the compositions of this invention are exemplified by a preferred maleimide, N-(2-methylnaphtyhl) maleimide.

The microbiocidal compounds useful in the practice of this invention which are isoindole dicarboximides having a sulfur atom bonded to the nitrogen atom of the dicarboximide group are compounds which contain at least one group having the structure:

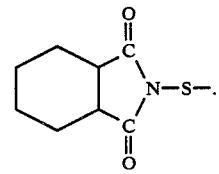

preferred isoindole dicarboximides are the following:

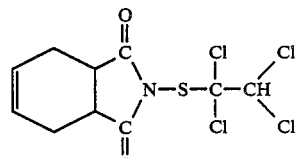

bis-N—[(1,1,2,2-tetrachloroethyl)thio]-4-cyclohexene-1,2-dicarboximide;

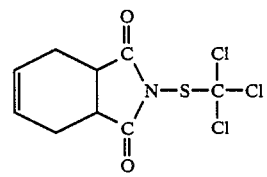

N—trichloromethylthio-4-cyclohexene-1,2-dicarboximide;

and

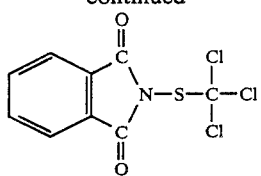

N—trichloromethylthio phthalimide.

The halogenated aryl alkanols which can be used as microbiocidal compounds in accordance with this invention are exemplified by a preferred compound, 2,4-dichlorobenzyl alcohol.

An example of a preferred isothiazolinone compound useful in the composition of this invention is 2-(n-octyl-4-isothiazolin-3-one).

The most preferred microbiocidal compounds are the bisphenoxarsines and bisphenarsazines having the formula:

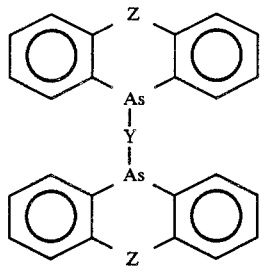

where Y is oxygen or sulfur and Z is oxygen or nitrogen. Of these bisphenoxarsines and bisphenarsazines, the most preferred are 10,10'-oxybisphenoxarsine; 10,10'-thiobisphenoxarsine; 10,10'-oxybisphenarsazine; and 10,10'-thiobisphenarsazine.

The stabilizing compositions in accordance with the invention are phenols which act as antioxidants, inhibiting UV-catalyzed oxidation of the microbiocides dissolved in cosolvents having alkanol moieties. Phenols are selected for their antioxidant properties and also for their compatibility with the polymer resin, the cosolvent and the microbiocide. The degree to which any phenol acts as an antioxidant must be emperically determined, as the relationship between phenol structure and oxidation-inhibiting properties is not fully understood at this time. Phenol, itself, is a suitable antioxidant. Nonyl phenol, which was previously used as a cosolvent for microbiocides and carriers, has some antioxidant properties, explaining why a solution of a microbiocide in nonyl phenol is resistant to UV-catalyzed oxidation; however, nonyl phenol as a minor additive to a primary solvent is generally insufficiently effective as an antioxidant.

Examples of suitable phenol antioxidants include:

Bisphenol A [4,4'-(1-methylethylidene)bisphenol];
Bisphenol B [4,4'-(1-methylpropylidene)bisphenol];

2,6-Di-t-butyl-4-methylphenol

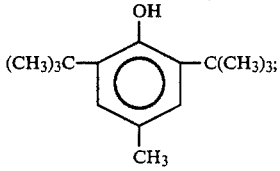

Styrenated phenols

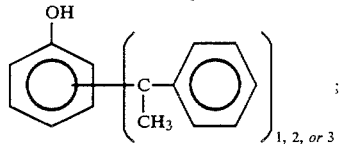

2- and 3-t-butyl-4-methoxyphenol

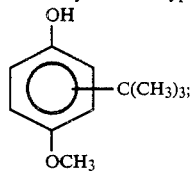

Alkylated hindered phenols

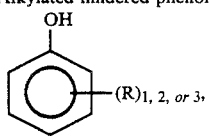

wherein, R's may be methyl of other alkyl groups, the larger ones usually being tertiary; frequently more than one type of group is present;

4-(hydroxymethyl)-2,6-di-t-butylphenol

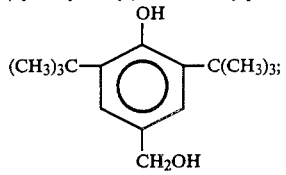

fortified hindered phenols such as those sold under the tradename Vanox ZS by Vanderbilt;

2,6-Di-t-butyl-4-sec-butylphenol

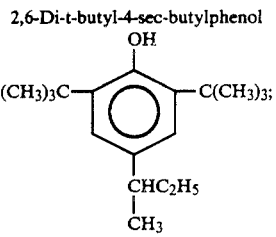

2,2'-methylenebis(4-methyl-6-t-butylphenol)

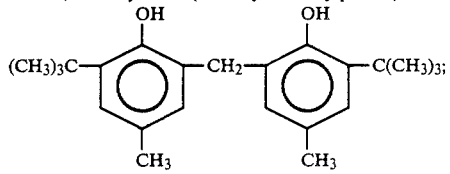

2,2'-methylenebis(4-ethyl-6-t-butylphenol)

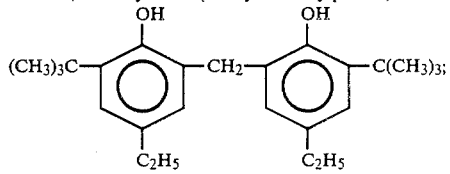

4,4'-methylenebis(2,6-di-t-butylphenol)

-continued 2,2'-ethylidenebis(4,6-di-t-butylphenol);

2,2'-methylenebis(4-methyl-6-(1-methylcyclohexyl) phenol)

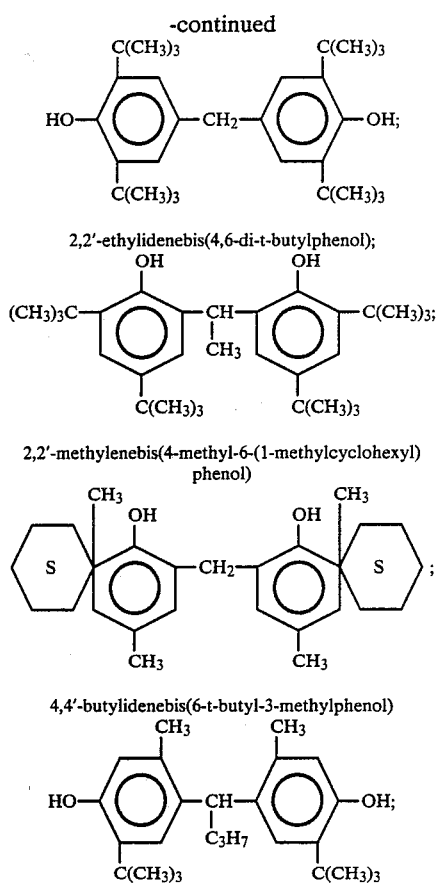

4,4'-butylidenebis(6-t-butyl-3-methylphenol)

Polybutylated Bisphenol A;

4,4'-thiobis(6-t-butyl-3-methylphenol)

4,4'-Methylenebis(2,6-dimethylphenol)

1,1'-Thiobis(2-naphthol)

methylene bridged polyalkylphenol, such as that sold under the trade name Ethyl Antioxidant 738 by Ethyl;

2,2'-thiobis(4-methyl-6-t-butylphenol)

-continued

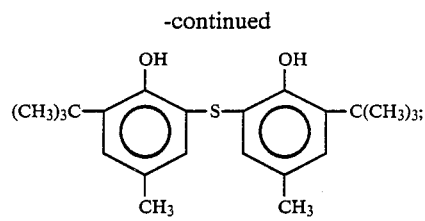

Sulfur containing hindered phenol cyanurate such as that sold under the trade name SAO-44 by Southland;

2,2'-isobutylidenebis(4,6-dimethylphenol)

2,2'-methylenebis(4-methyl-6-cyclohexylphenol)

butylated reaction product of p-cresol and dicyclopentadiene, average molecular weight 600–700, sold under the trade name Wingstayl by Goodyear;

tetrakis(methylene(3,5-di-t-butyl-4-hydroxyhydrocinnamate))methane $$C \left[ CH_2-O-\underset{\underset{O}{\|}}{C}-(CH_2)_2-\underset{C(CH_3)_3}{\overset{C(CH_3)_3}{\bigcirc}}-OH \right]_4 ;$$

1,3,5-trimethyl-2,4,6-tris(3,5-di-t-butyl-4-hydroxybenzyl)-benzene

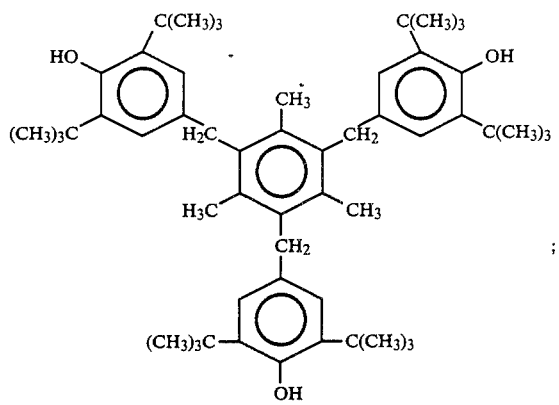

1,3,5-tris(3,5-di-t-butyl-4-hydroxybenzyl)
isocyanurate

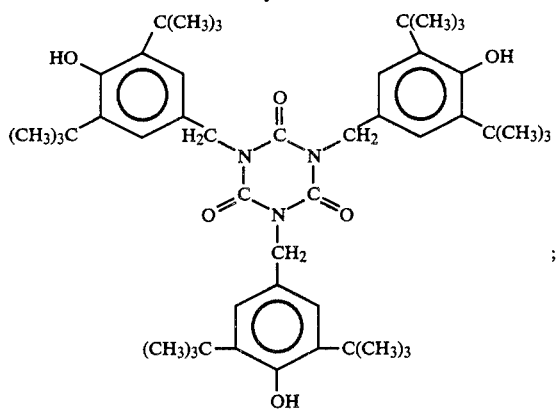

3:1 condensate of 3-methyl-6-t-butylphenol with crotonaldehyde sold under the trade name Topanol CA by ICI;

2,4-bis(n-octylthio)6-(4-hydroxy-3,5-di-t-butylanilino) 1,3,5-triazine

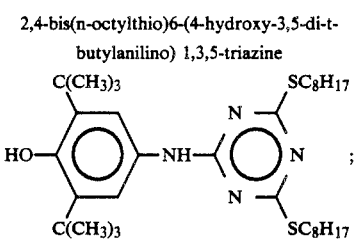

phenol/aldehyde condensates sold under the trade name Permanax EXP and Permanax WMP by Vulnax;

2,5-di-t-amylhydroquinone

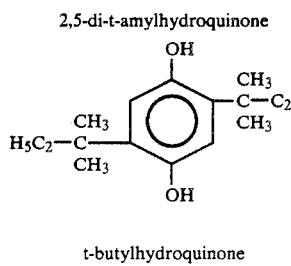

t-butylhydroquinone

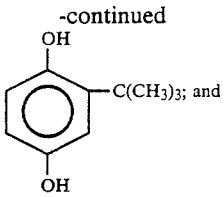

alkylated hydroquinone (structure not disclosed) sold under the trade name Antioxidant 451 by Uniroyal.

The microbiocidal solutions or liquid compositions useful in this invention should be employed in an amount at least sufficient to impart microbiocidal properties to the polymer composition or material containing them. This amount can vary widely depending upon the particular microbiocidal compound employed, the other components of the polymer composition in which it is employed, the environment in which the polymer composition will function and several other factors. The minimum amount of microbiocidal compound employed in a polymer composition is determined by what is known in the art as its Minimum Inhibitory Concentration (MIC). The maximum amount of microbiocidal compound which can be employed in a polymer composition is determined only by the amount of microbiocidal compound which can be uniformly incorporated into a particular polymer composition without adversely affecting the physical properties of the polymer composition. In general, the polymer compositions of this invention which possess microbiocidal properties contain from about 50 parts per million (ppm) to about 10,000 ppm, preferably about 100 ppm to 500 ppm, of microbiocidal compound. Phenoxarsine and phenarsazine compounds, the preferred microbiocidal compounds in accordance with this invention, are used at levels of between about 100 and about 5000 ppm (based upon the total weight of the polymer composition) and preferably between about 300 and about 1000 ppm.

The liquid microbiocidal solutions of this invention preferably contain much more microbiocidal compound than would be necessary simply to impart the desired microbiocidal properties to them. This is also true for the carrier-containing liquid compositions. These solutions and liquid compositions preferably contain large amounts of microbiocidal compound because they are advantageously employed as "concentrates" to produce polymer compositions which have lower concentrations of microbiocidal compounds, but still have the desired degree of microbiocidal activity. For example, the liquid microbiocidal solutions may contain from about 0.1 to about 30 weight percent microbiocidal compound (based on total solution weight). However, a solution containing, for example, 25% microbiocidal compound may be used to prepare a carrier-containing liquid composition which contains only about 5% microbiocidal compound, which carrier-containing liquid composition may, in turn, be used to prepare a polymer composition containing only 100 to 500 ppm microbiocidal compound.

The microbiocidal solutions of this invention (comprising the microbiocidal compound, the alkanol moiety-containing cosolvent, and the phenolic antioxidant) may be employed as additives for polymer compositions to impart microbiocidal properties to the polymer compositions. They may be added either directly to the polymer composition or they may be first incorporated into a carrier, such as a plasticizer or other polymer processing aid, by which the microbiocidal solutions are then incorporated into the polymer composition. When the latter manner is chosen, the carrier may be any of a variety of materials which are compatible with the polymeric resin and microbiocidal solution, e.g., the microbiocidal compound does not precipitate or otherwise separate from the cosolvent when incorporated into a polymeric resin along with the carrier. Examples of suitable carriers include, but are not limited to, plasticizers, and lubricants. Specific examples of carriers include, but are not limited to, typical plasticizers such as tricresyl phosphate, dipropylene glycol dibenzoate, diphenylcresyl phosphate, dipropylene glycol dibenzoate, diphenylcresyl phosphate, epoxidized soya, epoxidized tallate, dioctyl azelate, di(2-ethyl hexyl) phthalate, alkyl aryl phosphates, diisobutyl phthalate, diisodecyl phthalate, hydrogenated methyl rosin ester, n-octyl n-decyl phthalate, mixed n-alkyl phthalates, butyl benzyl phthalate, di-n-octyl phthalate, di-n-decyl phthalate, 3,4-epoxycyclohexyl methyl 3,4-epoxycyclohexane carboxylate, trioctyl trimellitate and low molecular weight polymeric plasticizers, such as Paraplex G-30 plasticizer sold by Rohm & Haas Co. and the like. Of these plasticizers, di(2-ethyl hexyl) phthalate, diisodecyl phthalate, butyl benzyl phthalate and epoxidized soya are preferred. Other polymer processing aids useful as carriers in accordance with this invention include, but are not limited to, polypropylene glycol; 1,4-butanediol; silicone oils such as polydimethylsiloxane; and methyl ethyl ketone.

As previously indicated, the concentration of microbiocidal compound in the microbiocidal solution may be sufficiently high that the carrier-containing composition prepared from the microbiocidal solution will, in turn, contain enough microbiocidal compound that, when the carrier-containing composition is added to a polymeric resin, the ultimately-formed polymer composition and articles prepared therefrom will have microbiocide properties. A cosolvent employed in the practice of the present invention is selected which solubilizes a sufficient concentration of a microbiocide compound so that either the solution or a carrier-containing concentrate composition which incorporates the solution when added to a polymeric resin at a specific amount relative to the resin, provides the desired end-use concentration of the microbiocide compound in the polymer composition.

It is generally a problem to solubilize sufficiently high concentrations of commonly used microbiocides in cosolvents. Generally, the higher the concentration of a microbiocidal compound dissolved in a cosolvent, the better, whether the solution is to be incorporated first into a carrier-containing composition and added as such to the polymeric resin (the more usual case) or the solution is to be incorporated directly into the polymeric resin. Generally, the cosolvent used to carry the microbiocidal compound into the carrier-containing concentrate composition and into the polymeric resin serves little or no beneficial function in the final polymeric composition and may even be detrimental if present in too high a concentration. If the solution is to be first admixed with a carrier to form a concentrate composition, the concentrate composition should contain the correct amount of microbiocide that when the carrier, e.g., plasticizer, is employed at optimal amounts, the carrier-containing concentrate composition provides the correct amount of microbiocidal compound to the end-use polymer composition. At the other extreme, a solution should not be too highly concentrated in microbiocidal compound, lest mixing problems be encountered; however, with the case of most microbiocides, obtaining a sufficiently high concentration of microbiocides is the major problem—not providing too high a concentration. For example, using solvents such as nonyl phenol, it was, heretofore, difficult to provide concentrate compositions which contained more than 2% OBPA by weight. When one considers that only a given amount of any carrier, such as a plasticizer, might be incorporated into a polymeric composition, if such a concentrate were the only source of microbiocidal compound to the final polymer composition, sub-optimal levels of microbiocides in the polymer composition were sometimes used. Using cosolvents having alkanol moieties as described above, OBPA-containing plasticizing compositions containing 5% and upwards by weight have been produced.

High concentrations of microbiocide compounds, both in solutions and in carrier-containing concentrate compositions, are desirable in other ways too. Less material, e.g., cosolvent, is required. Shipping and handling cost savings are also realized because less material must be shipped and stored.

While several advantages accrue by using alkanol moiety-containing cosolvents which solubilize relatively high concentrations of microbiocide compounds, the problem of UV-induced oxidation, discussed above, has been noted. Thus, in accordance with the present invention, microbiocide-containing solutions and carrier-containing concentrate compositions, in accordance with the invention, are provided with a phenol antioxidant. Generally such phenol antioxidant is provided at between about 2 and about 30 wt. percent relative to the primary alkanol moiety-containing cosolvent and preferably between about 3 and about 15 wt. percent. Thus, a solution in accordance with the present invention comprises between about 10 and about 30 wt. percent of a microbiocide compound, between about 70 and about 80 wt. percent of a cosolvent having an alkanol moiety and between about 1 and about 10 wt. percent of a phenolic antioxidant. The phenolic antioxidant itself has some solubilizing effect on the microbiocide compound, but generally less than the selected cosolvent. Also, the phenolic antioxidant is preferably employed at a much lower level than the primary cosolvent; thus, the phenolic compound is considered, for purposes of this invention, to be primarily an antioxidant, rather than a solvent or cosolvent.

In compositions in accordance with the present invention, the cosolvent typically comprises between about 2 and about 30 wt. percent of the composition as a whole and preferably between about 4 and about 20 wt. percent. The phenolic antioxidant typically comprises between about 0.1 and about 5 wt. percent of the concentrate composition and preferably between about 0.5 and about 1 wt. percent of the concentrate composition. The microbiocide typically comprises between about 0.5 and about 10 wt. percent of the concentrate composition and preferably between about 1 and about 5 wt. % of the concentrate composition. The balance is one or more carriers.

The concentrate composition containing carrier, cosolvent, phenolic antioxidant and microbiocide is generally added to a polymeric resin at a weight ratio of between about 1:100 and about 1:20. Solutions of cosolvent, microbiocide and phenolic antioxidant, free of carrier, are generally added to polymeric resins at weight ratios of between about 1:500 and about 1:100.

The polymers employed in the processes and products of this invention cover a wide variety of materials. In general, they include thermoplastic and thermosetting polymers, elastomers and other materials commonly known as "plastics". Other organic materials, for instance, naturally occurring materials, such as natural rubbers, cellulose and the like, are considered full equivalents of the "polymers" of this invention and should be included within that term. Examples of the polymers useful in the practice of this invention include, but are not limited to vinyl resins (such as those made from vinyl chloride and/or vinyl esters), polyolefins (such as polyethylene and polypropylene), elastomeric polyurethanes, nylon, polystyrene, polyesters (such as polyethylene terephthalate), polycarbonates, acrylonitrile-butadiene-styrene (ABS) copolymers, SBR rubbers, styrene-acrylonitrile copolymers, acrylic polymers, thermosetting polyurethanes (such as those used for foams and coatings), phenolic resins, silicone rubbers, natural rubber, EDPM polymers, cellulose and its derivatives, epoxy resins and various latexes.

The microbiocidal solutions of this invention can be prepared by simply adding the desired amount of microbiocidal compound to the alkanol moiety-containing cosolvent, heating (if necessary) the resulting mixture to a temperature which will cause the microbiocidal compound to dissolve, and maintaining that temperature until all of the microbiocidal compound dissolves. The resulting solution can then be cooled to room temperature. In this manner, stable microbiocidal solutions, i.e., those wherein no significant amount of microbiocidal compound precipitates from the solution upon cooling to room temperature, can be formed containing up to about 30% by weight microbiocidal compound based on the weight of the resulting microbiocidal solution.

The carrier-containing compositions of the present invention may be prepared by merely adding the carrier to a microbiocidal solution, prepared as described above, and mixing at room temperature until a uniform solution results. Alternatively, all ingredients of the carrier-containing composition (microbiocidal compound, solvent and polymer processing aid) can be mixed togetherand heated (if necessary) until the microbiocidal compound dissolves.

The microbiocidal solutions of this invention can be used to impart microbiocidal properties to polymer compositions. This can be done by simply adding the microbiocidal solution, either alone or as part of a carrier-containing composition, to the polymer composition by any of several convenient methods known in the art. Thus for instance, the polymer resin can be melted and the microbiocidal solution or carrier-containing composition added to and mixed with it (as in an extruder). Alternatively, the polymetric risin can be softened with or dissolved in a solvent and the microbiocidal solution or carrier-containing composition added to and mixed therewith.

The following examples illustrate the present invention, and are not intended to limit the invention or its scope in any manner. As used in the examples and throughout this specification, all parts and percentages are by weight unless otherwise indicated.

EXAMPLE 1

Stability of OBPA stored and/or treated in various manners was examined. Formulations stored in metal containers for a period of at least six months were examined for OBPA content and for phenoxarsenous acid (PAA) content, PAA being a degradation product of OBPA. The results are given in Table 1A below:

TABLE 1A

| Plasticizer | Plasticizer Wt. % | % OBPA | % PAA |
|---|---|---|---|
| ESO | | 4.91 | 0.15 |
| PG | | 4.75 | 0.026 |
| DOP | | 4.84 | 0.044 |
| DIDP | | 4.81 | 0.058 |

ESO = epoxidized soya oil;
PG = polypropylene glycol;
DOP = dioctylphthalate; and
DIDP = diisodecylphthalate In a plasticizer, OBPA undergoes some, though relatively little degredation when stored in the dark.

1% solutions of OBPA were prepared in benzyl alcohol (BzAlc), isodecyl alcohol (IDA) and nonyl phenol (NP). The solutions were exposed to a source of UV light for a period of four hours. OBPA and PAA were analyzed both before and after UV exposure. The results are as follows in Table 1B:

TABLE 1B

| Solvent | % OBPA before UV | % OBPA after UV | % PAA before UV | % PAA after UV |
|---|---|---|---|---|
| BzAlc | 1.02 | (less than 0.02) | 0.012 | 1.17 |
| IDA | 1.08 | 0.68 | 0.005 | 0.45 |
| NP | 1.08 | 1.07 | 0.005 | 0.011 |

This experiment shows that whereas nonyl phenyl apparently blocks UV catalyzed degredation of OBPA, UV-catalyzed oxidation of OBPA occurs rapidly in IDA and quite rapidly in BzAlc.

Formulations containing 95% (DOP) plasticizer, approximately 1% OBPA and various plasticizers were exposed to UV light and anaylzed for OBPA and PAA both before and after UV exposure. The results are as follows in Table 1C:

TABLE 1C

| | % DOP | Cosolvent | % Cosolvent | OBPA % before UV |
|---|---|---|---|---|
| A | 95 | BzAlc | 4 | 0.89 |
| B | 95 | IDA | 4 | 0.90 |
| C | 95 | NP | 4 | 0.90 |
| D | 99 | None | — | 1.06 |

| | OBPA % after UV | PAA % before UV | PAA % after UV |
|---|---|---|---|
| A | 0.42 | 0.059 | 0.076 |
| B | 0.73 | 0.021 | 0.031 |
| C | 0.81 | 0.086 | 0.16 |
| D | 0.84 | 0.013 | 0.13 |

The results with plasticized formulations are similar to the results in cosolvent alone, namely that whereas NP tends to stabilize OBPA against UV-catalyzed degredation, IDA and especially BzAlc destabilize OBPA. This experiment demonstrates the problem which the invention is intended to overcome.

EXAMPLE 2

Samples of 400 gms each were prepared according to the formulations in Table 2A below. Oxygen-rich DIDP was prepared by bubbling air through the DIDP for 24 hours. Oxygen-deficient DIDP was prepared by bubbling nitrogen through the DIDP for 24 hours. The two types of DIDP used electrical grade (containing 0.6% Bisphenol A antioxidant) and non-electrical grade (no Bisphenol A).

All samples were divided into 4 stress groups:
A=Room temperature aging in the dark
B=Exposure to overhead lighting
C=Heat aged at 120° F. for 2 weeks
D=Subjected to 5 freeze/thaw cycles Room temperature storage (A) an freeze-thaw cycles (D) had little effect on OBPA stability and will not be discussed further.

TABLE 2A

| Sample | % OBPA | % Benzyl Alcohol | % DIDP | DIDP Type | % Benz Aldehyde |
|---|---|---|---|---|---|
| 1 | 2 | 8 | 89 | ++ | 1 |
| 2 | 2 | 8 | 89 | +− | 1 |
| 3 | 2 | 8 | 90 | ++ | 0 |
| 4 | 2 | 8 | 90 | +− | 0 |
| 5 | 2 | 8 | 89 | −+ | 1 |
| 6 | 2 | 8 | 89 | −− | 1 |
| 7 | 2 | 8 | 90 | −+ | 0 |
| 8 | 2 | 8 | 90 | −− | 0 |

++ Is with oxygen and with Bisphenol A.
+− Is with oxygen and without Bisphenol A.
−+ Is without oxygen and with Bisphenol A.
−− Is without oxygen and without Bisphenol A.

Table 2B below shows the results of overhead lighting on the OBPA formulations:

TABLE 2B

EXPOSURE TO OVERHEAD LIGHTING

| SAMPLE | % OBPA | % BENZ ALC. | % BENZ ALDEHYDE | DIDP TYPE |
|---|---|---|---|---|
| 1B | 2 | 8 | 1 | ++ |
| 2B | 2 | 8 | 1 | +− |
| 3B | 2 | 8 | 0 | ++ |
| 4B | 2 | 8 | 0 | +− |
| 5B | 2 | 8 | 1 | −+ |
| 6B | 2 | 8 | 1 | −− |
| 7B | 2 | 8 | 0 | −+ |
| 8B | 2 | 8 | 0 | −− |

| SAMPLE | % OBPA INITIAL | % OBPA 1 Mo. UV | % OBPA 2 Mos. UV | % PAA INITIAL |
|---|---|---|---|---|
| 1B | 1.91 | 1.73 | 1.62 | 0.007 |
| 2B | 1.95 | 1.58 | 1.56 (CRYSTALS) | 0.010 |
| 3B | 1.98 | 1.76 | 1.77 | 0.006 |
| 4B | 1.91 | 1.52 | 1.44 (CRYSTALS) | 0.007 |
| 5B | 1.92 | 1.73 | 1.79 | 0.007 |
| 6B | 1.95 | 1.75 | 1.82 | 0.008 |
| 7B | 1.97 | 1.87 | 1.74 | 0.007 |
| 8B | 1.92 | 1.72 | 1.67 | 0.006 |

| SAMPLE | % PAA 1 MO. UV | % PAA 2 MOS. UV | % BzAlc INITIAL | % BzAlc 1 MO. UV |
|---|---|---|---|---|
| 1B | 0.220 | 0.390 | 8.00 | 7.87 |
| 2B | 0.320 | 0.310 | 8.06 | 7.93 |
| 3B | 0.094 | 0.210 | 8.19 | 7.80 |
| 4B | 0.320 | 0.290 | 8.09 | 7.70 |
| 5B | 0.077 | 0.120 | 7.75 | 7.80 |
| 6B | 0.051 | 0.091 | 8.03 | 7.93 |
| 7B | 0.086 | 0.220 | 8.06 | 7.97 |
| 8B | 0.230 | 0.270 | 7.84 | 7.89 |

| SAMPLE | % BzAld INITIAL | % BzAld 1 MO. UV |
|---|---|---|
| 1B | 0.93 | 0.920 |
| 2B | 0.93 | 0.890 |
| 3B | nd | 0.023 |
| 4B | nd | 0.047 |
| 5B | 0.89 | 0.950 |
| 6B | 0.91 | 0.960 |
| 7B | nd | 0.024 |
| 8B | nd | 0.038 | nd = none detected

The following observations can be made with respect to light exposure:
Crystals were only present in oxygenated/non-electrical grade samples which further had lowest OBPA levels (ca 25% loss).
Oxygen-rich samples had a lower OBPA and higher PAA than those that were oxygen deficient.
Samples with Bisphenol A had lower PAA levels than samples without Bisphenol A (OBPA loss is only about 10%).
The benzaldehyde spike had a negligable effect on all samples.

The effects of heat aging are given in Table 2C below:

TABLE 2C

2 WEEKS HEAT AGING AT 130° F.

| SAMPLE | % OBPA | % BENZ. ALC. | % BENZ ALDEHYDE | DIDP TYPE |
|---|---|---|---|---|
| 1C | 2 | 8 | 1 | ++ |
| 2C | 2 | 8 | 1 | +− |
| 3C | 2 | 8 | 0 | ++ |
| 4C | 2 | 8 | 0 | +− |
| 5C | 2 | 8 | 1 | −+ |
| 6C | 2 | 8 | 1 | −− |
| 7C | 2 | 8 | 0 | −+ |
| 8C | 2 | 8 | 0 | −− |

| SAMPLE | % OBPA INITIAL | % OBPA FINAL | % PAA INITIAL | % PAA FINAL |
|---|---|---|---|---|
| 1C | 1.91 | 1.90 | 0.007 | 0.007 |
| 2C | 1.95 | 1.71 | 0.010 | 0.320 |
| 3C | 1.98 | 1.87 | 0.006 | 0.006 |
| 4C | 1.91 | 0.86 | 0.007 | 1.130 |
| 5C | 1.92 | 1.92 | 0.007 | 0.005 |
| 6C | 1.95 | 1.87 | 0.008 | 0.006 |
| 7C | 1.97 | 1.88 | 0.007 | 0.007 |
| 8C | 1.92 | 1.85 | 0.006 | 0.006 |

| SAMPLE | % BzAlc INITIAL | % BzAlc FINAL | % BzAld INITIAL | % BzAld FINAL |
|---|---|---|---|---|
| 1C | 8.00 | 7.99 | 0.93 | 0.970 |
| 2C | 8.06 | 8.02 | 0.93 | 0.970 |
| 3C | 8.19 | 7.96 | nd | 0.001 |
| 4C | 8.09 | 7.96 | nd | 0.200 |
| 5C | 7.75 | 8.06 | 0.89 | 0.930 |
| 6C | 8.03 | 8.11 | 0.91 | 0.930 |
| 7C | 8.06 | 8.06 | nd | 0.002 |
| 8C | 7.84 | 8.10 | nd | 0.002 | nd = none detected

The following observation may be made about heat aging:
Oxygen-rich, non-electrical grade DIDP showed a dramatic increase in PAA percentage plus the formation of crystals. However, all remaining samples showed no increase in PAA.

In summary, OBPA in solution is subject to oxidation. Oxidation of OBPA is dramatically increased by exposure to light, indicating UV-catalyzer oxidation. The presence of a phenolic antioxidant, in accordance with the invention inhibits oxidation of OBPA, including UV-catalyzed oxidation of OBPA.

While the invention has been described in terms of certain preferred embodiments, modifications obvious to one with ordinary skill in the art may be made without departing from the scope of the present invention.

Various features of the invention are set forth in the following claims.

What Is Claimed:

1. A concentrate solution comprising between about 10 and about 30 wt. percent of a microbiocide, between about 70 and about 80 wt. percent of a solvent for said microbiocide having an alkanol moiety and between about 1 and about 10 wt. percent of a phenol antioxidant, based upon the total combined weight of microbiocide, solvent and phenolic antioxidant.

2. A solution according to claim 1 wherein said microbiocide is a phenoxarsine or a phenarsazine.

3. A solution according to claim 1 wherein said solvent is benzyl alcohol.

4. A composition comprising between about 0.5 and about 10 wt. percent of a microbiocide, between about 2 and about 30 wt. percent of a cosolvent for said microbiocide having an alkanol moiety, between about 0.1 and about 5 wt. percent of a phenolic antioxidant, and balance one or more carriers.

5. A concentrate composition according to claim 4 wherein said carrier comprises a plasticizer for a polymer.

6. A concentrate composition according to claim 5 wherein said plasticizer is a plasticizer for a halogen-containing polymer.

7. A concentrate composition according to claim 4 wherein said microbiocide is selected from the group consisting of phenoxarsines and phenarsazines.

8. A concentrate composition according to claim 7 wherein said microbiocide is selected from the group consisting of 10,10'-oxybisphenoxarsine; 10,10'-thiobisphenoxarsine; 10,10'-oxybisphenarsazine and 10,10'-thiobisphenarsazine.

9. A concentrate according to claim 4 wherein said phenolic antioxidant is selected from the group consisting of phenol, Bisphenol A, Bisphenol B, and mixtures thereof.

10. A concentrate according to claim 4 wherein said microbiocide is selected from the group consisting of maleimides, isoindole dicarboximides having a sulfur atom bonded to the nitrogen atom of the dicarboximide group, halogenated aryl alkanols, and isothiazolinone compounds.

11. A concentrate according to claim 10 wherein microbiocide is selected from the group consisting of N-(2-methylnaphthyl) maleimide; bis-N-[1,1,2,2tetrachloroethyl)thio]4-cyclohexene-1,2-dicarboximide; N-trichloromethylthio-4-cyclohexene-1,2-dicarboximide; N-trichloromethylthio phthalimide; 2,4-dichlorobenzyl alcohol; and 2-(n-octyl-4-isothiazolin-3-one).

12. A concentrate according to claim 4 wherein said cosolvent is an aryl alkanol.

13. A concentrate according to claim 4 wherein said cosolvent is a straight or branched chain, saturated or unsaturated alcohol having a chain of at least 8 carbon atoms.

14. A concentrate composition according to claim 4 wherein said cosolvent is benzyl alcohol.

15. A solution according to claim 1 wherein said solvent is isodecyl alcohol.

16. A solution according to claim 2 wherein said solvent is benzyl alcohol.

17. A solution according to claim 2 wherein said solvent is isodecyl alcohol.

18. A solution according to claim 1 wherein said microbiocide is selected from the group consisting of 10,10'-oxybisphenoxarsine; 10,10'-thiobisphenoxarsine; 10,10'-oxybisphenarsazine; and 10,10'-thiobisphenarsazine.

19. A solution according to claim 3 wherein said microbiocide is selected from the group consisting of 10,10'-oxybisphenoxarsine; and 10,10'-thiobisphenoxarsine;

20. A solution according to claim 1 wherein said phenolic antioxidant is selected from the group consisting of phenol, Bisphenol A, Bisphenol B, and mixtures thereof.

21. A solution according to claim 2 wherein said phenolic antioxidant is selected from the group consisting of phenol, Bisphenol A, Bisphenol B, and mixtures thereof.

22. A solution according to claim 3 wherein said phenolic antioxidant is selected from the group consisting of phenol, Bisphenol A, Bisphenol B, and mixtures thereof.

23. A solution according to claim 1 wherein said microbiocide is 10,10'-oxybisphenoxarsine.

24. A solution according to claim 3 wherein said microbiocide is 10,10'-oxybisphenoxarsine.

25. A concentrate composition according to claim 5 wherein said plasticizer is selected from the group consisting of tricresyl phosphate, dipropylene glycol dibenzoate, diphenylcresyl phosphate, dipropylene glycol dibenzoate, diphenylcresyl phosphate, epoxidized soya, epoxidized tallate, dioctyl azelate, di(2-ethyl hexyl) phthalate, alkyl aryl phosphates, diisobutyl phthalate, diisodexyl phthalate, hydrogenated methyl rosin ester, n-octyl n-decyl phthalate, mixed n-alkyl phthalates, butyl benzyl phthalate, di-n-octyl phthalate, di-n-decyl phthalate, 3,4-epoxycyclohexyl methyl 3,4-epoxycyclohexane carboxylate, trioctyl trimellitate, polypropylene glycol, 1,4-butanediol, silicone oil, methyl ethyl keton, and mixtures thereof.

26. A concentrate composition according to claim 5 wherein said plasticizer is di-n-octyl phthalate.

27. A concentrate composition according to claim 5 wherein said plasticizer is diisodecyl phthalate.

28. A concentrate composition according to claim 5 wherein said plasticizer is di(2-ethyl hexyl) phthalate.

29. A concentrate composition according to claim 5 wherein said plasticizer is butyl benzyl phthalate.

30. A concentrate composition according to claim 5 wherein said plasticizer is epoxidized soya.

31. A concentrate composition according to claim 5 wherein said plasticizer is polypropylene glycol.

32. A concentrate composition according to claim 4 wherein said microbiocide is 10,10'-oxybisphenoxarsine.

33. A concentrate composition according to claim 5 wherein said plasticizer is n-alkyl phthalate or n-alkyl phthalate mixture.

34. A concentrate composition according to claim 5 wherein said plasticizer is 1,4 butanediol.

35. A concentrate composition according to claim 4 wherein said cosolvent is isodecyl alcohol.

* * * * *